United States Patent [19]
Yoshioka et al.

[11] Patent Number: 5,907,157
[45] Date of Patent: May 25, 1999

[54] METHOD AND APPARATUS FOR PREPARING SPECIMEN

[75] Inventors: Tadanori Yoshioka, Tachikawa; Mikio Naruse; Harumi Kihara, both of Tokyo, all of Japan

[73] Assignee: JEOL Ltd., Tokyo, Japan

[21] Appl. No.: 08/792,831

[22] Filed: Jan. 30, 1997

[30] Foreign Application Priority Data

Feb. 1, 1996 [JP] Japan ...................................... 8-16812

[51] Int. Cl.$^6$ .................................................. H01J 37/31
[52] U.S. Cl. ..................................... 250/492.2; 250/505.1
[58] Field of Search .................................. 250/397, 398, 250/492.2, 492.22, 505.1

[56] References Cited

U.S. PATENT DOCUMENTS

| | | | |
|---|---|---|---|
| 3,736,425 | 5/1973 | Chernow | 250/492.21 |
| 4,181,860 | 1/1980 | Sumi | 250/492.22 |
| 4,263,514 | 4/1981 | Reeds | 250/398 |
| 4,550,258 | 10/1985 | Omata et al. | 250/505.1 |
| 4,739,173 | 4/1988 | Blosser et al. | 250/505.1 |
| 4,899,060 | 2/1990 | Lischke | 250/505.1 |
| 5,166,531 | 11/1992 | Huntzinger | 250/505.1 |
| 5,180,919 | 1/1993 | Oae et al. | 250/398 |
| 5,364,718 | 11/1994 | Oae et al. | 250/492.22 |

FOREIGN PATENT DOCUMENTS

| | | |
|---|---|---|
| 4337445 | 11/1992 | Japan . |
| 4345740 | 12/1992 | Japan . |
| 528950 | 2/1993 | Japan . |

*Primary Examiner*—Bruce Anderson
*Attorney, Agent, or Firm*—Webb Ziesenheim Bruening Logsdon Orkin & Hanson, P.C.

[57] ABSTRACT

A method and apparatus for preparing a specimen adapted for electron microscopy comprises an evacuated specimen-processing chamber. A specimen having a surface to be processed is placed inside the processing chamber A beam-blocking member is placed close to the processed surface so as to block a part of an etching beam A first etching step is performed by directing the beam at the specimen via the blocking member. Then, the specimen and the blocking member are moved relative to each other. Finally, a second etching step is performed by directing the beam at the specimen via the blocking member. As a result, the specimen becomes a thin film and it can be observed with the electron microscope.

18 Claims, 16 Drawing Sheets

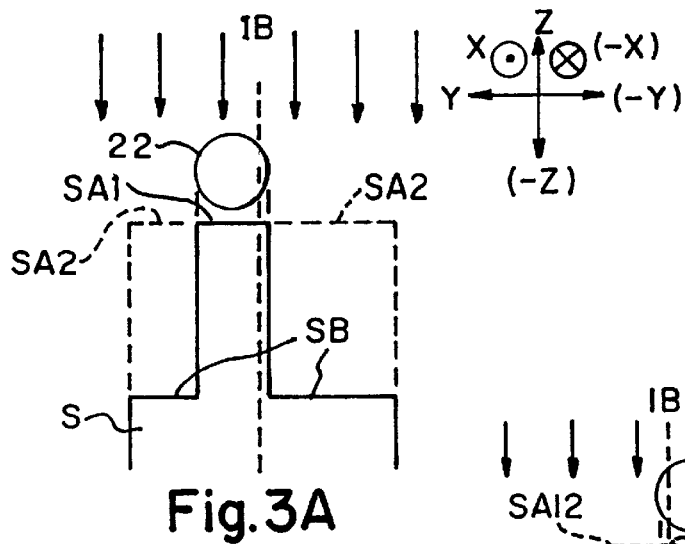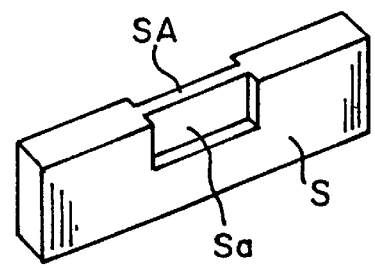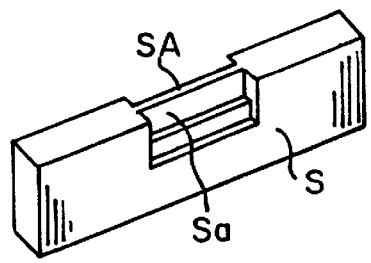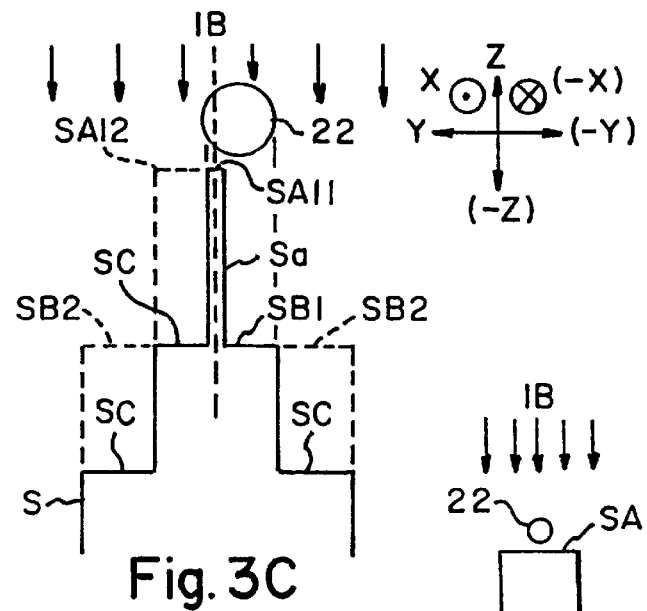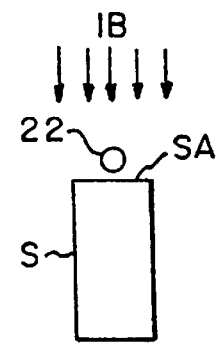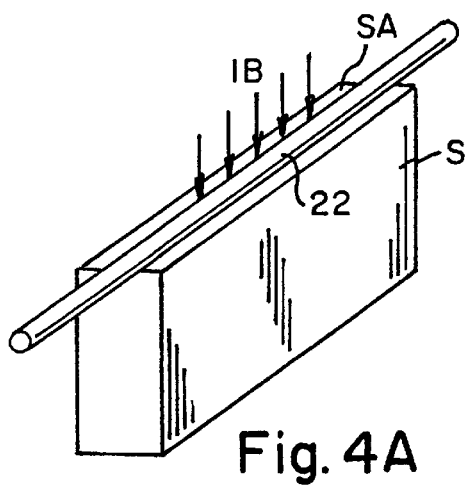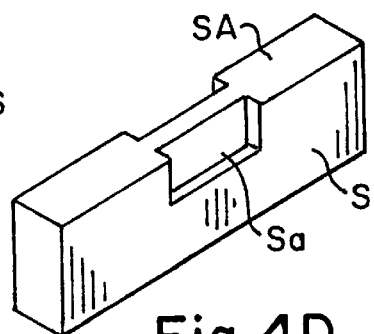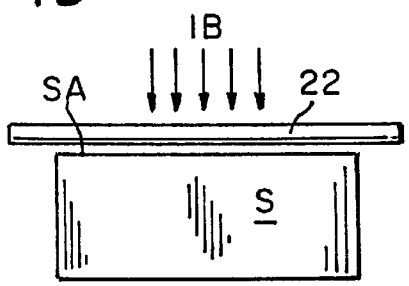

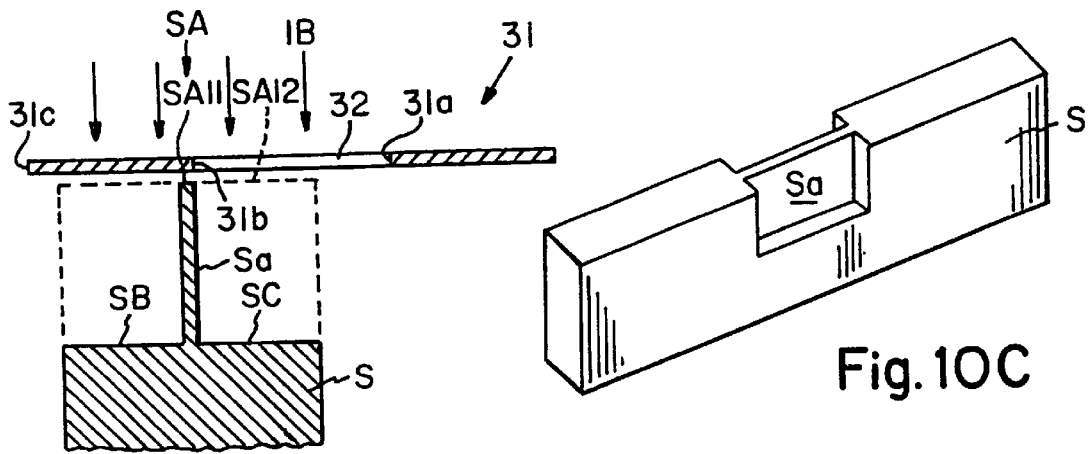
Fig.10B
Fig.10A
Fig.10C
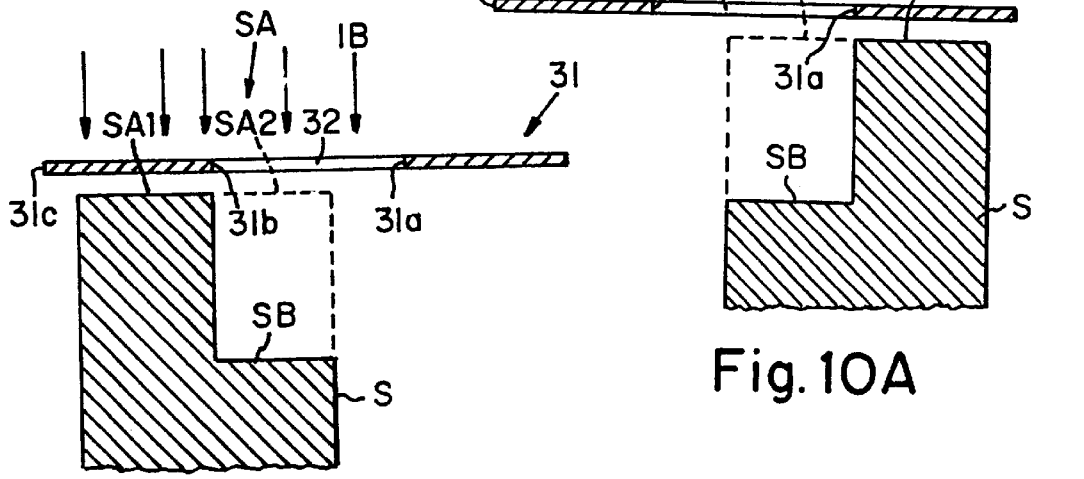
Fig.11A
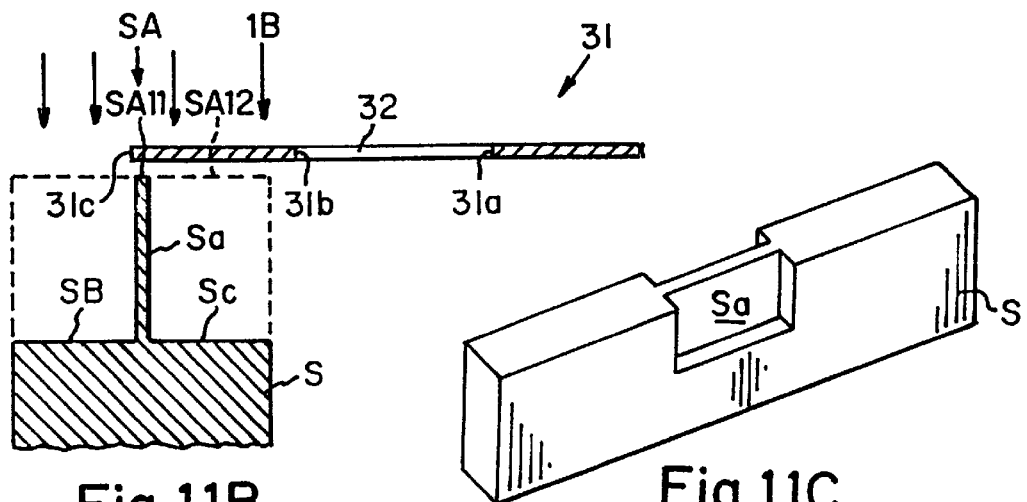
Fig.11B
Fig.11C

METHOD AND APPARATUS FOR PREPARING SPECIMEN

FIELD OF THE INVENTION

The present invention relates to a method and apparatus for preparing a specimen to be observed with a transmission electron microscope, scanning electron microscope, or other instrument.

BACKGROUND OF THE INVENTION

A transmission electron microscope (TEM) is an instrument for obtaining a TEM image of a specimen by directing an electron beam at the specimen and magnifying and projecting an electron image transmitted through the specimen, for example, onto a fluorescent screen. The thickness of the specimen observed with this transmission electron microscope is required to be less than 200 nm so that the electron beam can penetrate through the specimen. This specimen has been prepared by the prior art procedure described below.

It is assumed that an integrated circuit has been fabricated on a silicon wafer W. For example, when a cross section of this wafer taken in the direction (indicated by t) of the thickness is observed with a transmission electron microscope, the wafer is processed by the following sequence of steps:

(1) As shown in FIG. 25, a plurality of specimens S1 are cut out from the wafer W.

(2) As shown in FIGS. 26, (A) and (B), the extracted specimens S1 are stacked on top of each other in the direction of thickness indicated by t and glued together.

(3) As shown in FIGS. 26, (C) and (D), the glued specimens are cut into a cylinder having a diameter of about 3 mm.

(4) As shown in FIG. 26(E), the cylindrical specimen is sectioned into disks, each about 0.2 mm thick.

(5) Each specimen disk approximately 0.2 mm thick is thinned to a thickness of about 70 $\mu$m by a polishing machine. FIG. 26(F) shows a specimen polished to a thickness of approximately 70 $\mu$m.

(6) As shown in FIGS. 27, (A) and (B), the specimen with a dimpled center is polished while rotated. As a result, the thickness of the specimen taken in the center is about 10 $\mu$m.

(7) As shown in FIG. 27(C), an ion beam is made to impinge on the specimen at a shallow angle to polish the specimen surface with ions. Thus, the thickness of the specimen in the center is less than 200 nm. During observation of the specimen, an electron beam is directed at the center of the specimen thinned in this way.

The prior art specimen preparation work as described above needs sophisticated art. It takes a long time even for a skilled person to prepare the specimen by this technique. Furthermore, it is difficult to accurately bring a desired portion of the wafer W into the center of the specimen S and to thin it.

SUMMARY OF THE INVENTION

In view of the foregoing problems, the present invention has been made. It is an object of the present invention to provide an apparatus permitting one to easily and quickly prepare a specimen to be observed with a transmission electron microscope.

It is another object of the invention to provide a method of easily and quickly preparing a specimen to be observed with a transmission electron microscope.

It is a further object of the invention to provide a method and apparatus permitting one to precisely select a desired portion from a specimen and to thin it.

A method of preparing a specimen according to the present invention comprises the steps of: evacuating the interior of a specimen-processing chamber; placing a specimen in the specimen-processing chamber at a location where an etching beam impinges on the specimen; preparing a beam-blocking member having a first linear edge and a second linear edge which is substantially parallel to the first linear edge; placing the beam-blocking member close to a surface of the specimen to be processed such that the beam-blocking member blocks a part of the beam directed at the specimen; performing a first etching step by directing the beam at the specimen via the beam-blocking member to cause the first edge to create an irradiated region and a nonirradiated region on the specimen; producing a relative movement between the specimen and the beam-blocking member in such a way that the second edge is brought over the nonirradiated region; and then performing a second etching step by directing the beam at the specimen via the specimen-blocking member to create a protruded region that is put between a first boundary line and a second boundary line on the specimen The first boundary line is created by a contribution of the first edge, while the second boundary line is created by a contribution of the second edge.

A specimen preparation apparatus according to the invention comprises: a specimen-processing chamber whose interior is evacuated by a vacuum pump; a specimen stage on which a specimen to be placed in the specimen-processing chamber is placed; a beam generator for generating an etching beam to be directed at a surface of the specimen to be processed; a beam-blocking member having a first linear edge and a second linear edge which is substantially parallel to the first linear edge, the beam-blocking member being placed close to the processed surface of the specimen in such a way that the beam-blocking member blocks a part of the beam directed at the specimen; and a moving mechanism for producing a relative movement between the specimen and the beam-blocking member.

Other objects and features of the invention will appear in the course of the description thereof, which follows.

BRIEF DESCRIPTION OF THE DRAWINGS

FIGS. 3A–3D are diagrams illustrating the operation of the specimen preparation apparatus shown in FIG. 1 when it is used in one mode;

FIGS. 4A–4D are diagrams illustrating the operation of the specimen preparation apparatus shown in FIG. 1 when it is used in a different mode;

FIGS. 10A–10C are diagrams illustrating the operation of the apparatus shown in FIG. 9 when it is used in one mode;

FIGS. 11A–11C are diagrams similar to FIGS. 10A–10C, but in which the apparatus is used in a different manner;

DETAILED DESCRIPTION OF THE INVENTION

Figure 1:
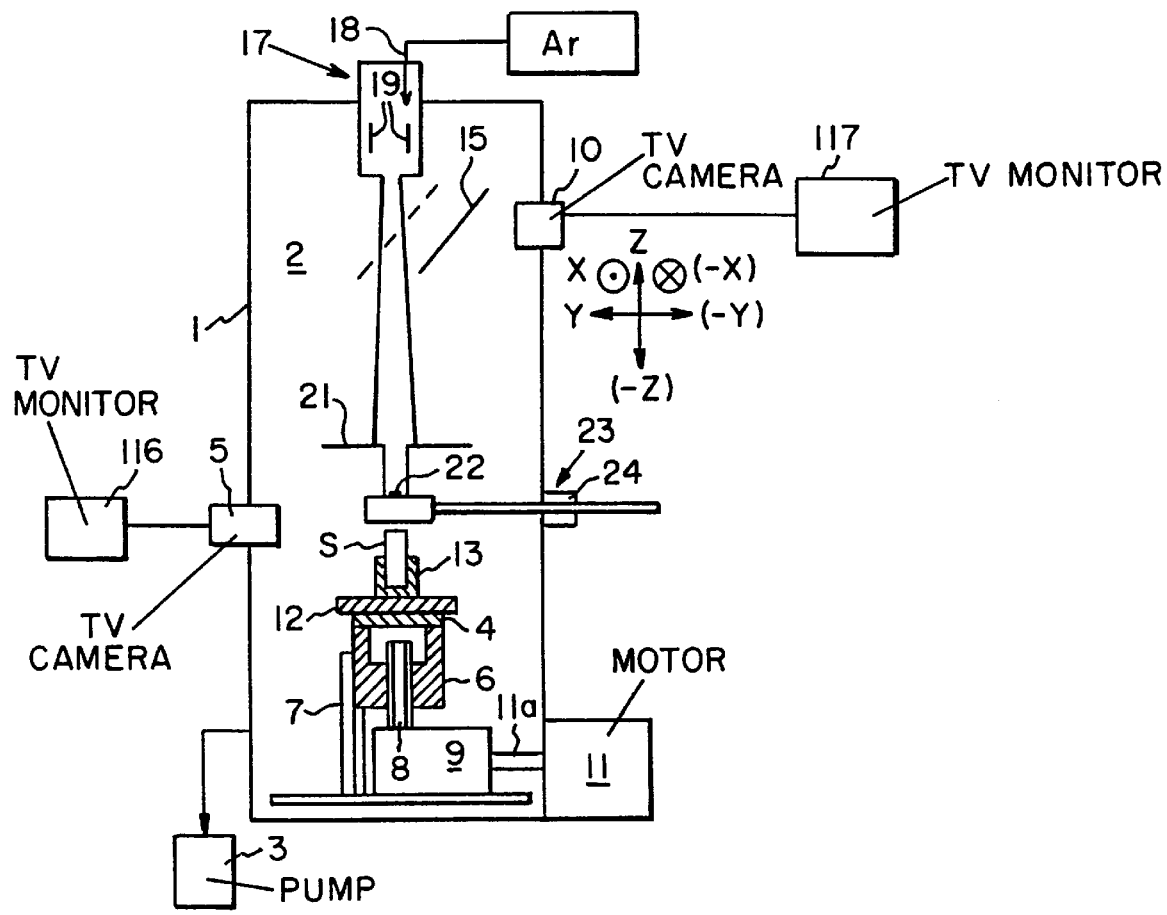
FIG. 1 is a schematic diagram of a specimen preparation apparatus according to the invention.
Figure 2:
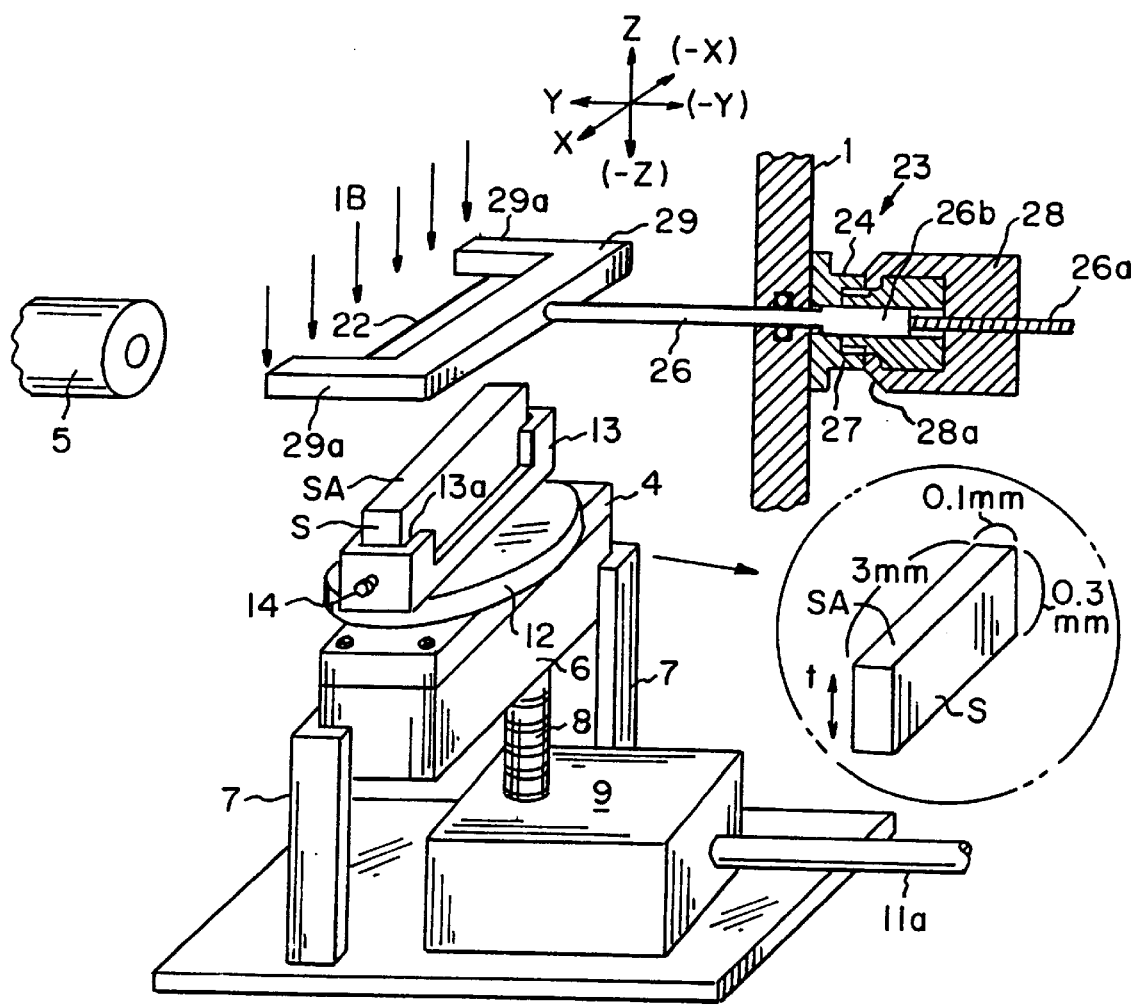
FIG. 2 is an enlarged perspective view of a holder for supporting a beam-blocking member and a specimen stage shown in FIG. 1.

A specimen preparation apparatus according to the present invention is next described by referring to FIGS. 1, 2, 3A, 3B, 3C, and 3D. In FIGS. 1 and 2, a specimen-processing chamber 2 is surrounded by a wall member 1. The interior of the chamber 2 is evacuated by a vacuum pump 3. A vertically movable table 4 is mounted inside the specimen-processing chamber 2 so as to be movable vertically, or along the Z-axis. The elevatable table 4 is mounted to the top surface of a nut block 6 into which a threaded shaft 8 is screwed. The elevatable table 4 is moved along the Z-axis by rotating the threaded shaft 8. A guide member 7 is mounted to inhibit rotation of the nut block 6 and to guide the nut block 6 when it moves along the Z-axis. A rotating force from an electric motor 11 is transmitted to the shaft 8 via a gearbox 9 to rotate the shaft 8.

A turntable 12 is rotatably held on the elevatable table 4 by a rotating means (not shown) A specimen stage 13 is supported on the turntable 12 and made of a boxlike member provided with a groove. The inner sidewall of the groove forms a specimen-holding portion 13a. A specimen S is held to this specimen-holding portion 13a. A plurality of screws 14 extend through the sidewall of the specimen-holding portion 13a to hold the specimen S to the specimen stage 13. For example, the specimen S held on the specimen stage 13 is a silicon wafer measuring 3 mm×0.1 mm×0.3 mm.

In this embodiment, the specimen S assumes a rodlike shape and has a side surface SA to be processed. This processed side surface SA extends longitudinally of the specimen. In order to hold the specimen S along the X-axis, the specimen stage 13 consisting of a grooved, boxlike member is elongated along the X-axis and is low in height.

Also, the specimen-holding portion 13a consisting of the inner sidewall defining the groove that is open at its upper side is elongated along the X-axis. The specimen S is held within the specimen-holding portion 13a such that the specimen extends along the X-axis.

An ion beam generator 17 is mounted at the top of the specimen-processing chamber 2. This generator 17 has a gas inlet portion 18 for admitting Ar gas and a discharge electrode 19 across which a high voltage is applied. The ion beam generator 17 produces Ar ions by an electric discharge. An aperture 21 is positioned below the ion beam generator 17 to reduce the ion beam diameter on the processed surface SA of the specimen down to about 1 mm. Neon, nitrogen, or other gas may be used as a discharge gas in the ion beam generator instead of the Ar gas. Furthermore, the diameter of the ion beam IB may be adjusted to a desired value with an appropriate focusing coil before the beam hits the processed surface of the specimen S.

A support device 23 which holds a linear beam-blocking member 22 is located between the aperture 21 and the specimen stage 13. The support device 23 has a micrometer 24 held to the chamber 1. This micrometer 24 comprises a movable rod 26, a guide member 27, and a knob 28. A micrometer screw 26a is formed at one end of the movable rod 26. A guided portion 26b of square cross section is mounted in the center of the movable rod 26. The guide member 27 holds the guided portion 26b of the rod 26 in such a way that it is capable of moving axially but incapable of rotating about the axis. The knob 28a is in mesh with the micrometer screw 26a. When the knob 28 is rotated, the movable rod 26 moves axially.

An inclined surface 28a is formed at the left end of the knob 28. A scale is formed on this inclined surface. A corresponding scale is formed on the outer surface of the guide member 27. The amount of movement of the movable rod 26 in the axial direction can be read from the amount of rotation between these two scales. A support arm 29 that holds the beam-blocking member 22 is mounted at an end of the movable rod 26. The left end of the arm 29, or the end in the Y-direction, is split into a pair of fixing portions 29a which are spaced from each other in the X-direction by a distance of about 10 mm. The beam-blocking member 22 is mounted to the bottom surfaces of the fixing portions 29a. The beam-blocking member 22 is made of a member of tungsten (W) enclosed in an amorphous metal layer. For instance, this amorphous metal layer is a nickel-phosphorus electroless plating. The cross section of the beam-blocking member 22 is circular in shape and has a diameter of approximately 50 $\mu$m. The cross section of the beam-blocking member 22 may also have a diameter of 10 $\mu$m to hundreds of micrometers. Furthermore, the cross section may be rectangular. The beam-blocking member 22 is mounted to the bottom surfaces of the fixing portions, because the specimen S is brought close to the beam-blocking member 22 such that their space is less than 10 $\mu$m to enhance the accuracy of etching described later. If the specimen S is small enough to pass between the fixing portions of the support arm 29, then the beam-blocking member 22 may be mounted to the top surfaces of the fixing portions.

TV cameras 5 and 10 are mounted to the inner walls of the chamber 1. The TV camera 5 is arranged in order to observe the beam-blocking member 22 from the sideward direction. The TV camera 10 is arranged in order to observe the beam blocking member 22 in the direction from the ion beam generator 17 via a mirror 15 which is removably inserted on the optical axis of the ion beam generator 17. Display devices 116 and 117 are connected with the TV cameras 5 and 10, respectively.

Figure 25:
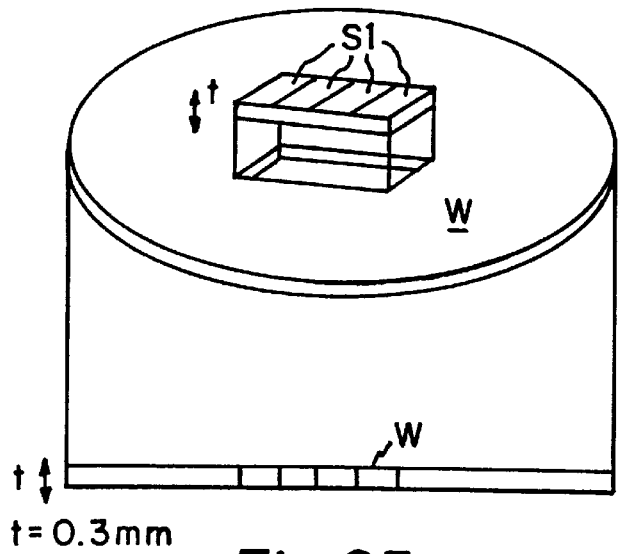
FIGS. 25–27 are views illustrating the prior art specimen preparation method.
Figure 26A:
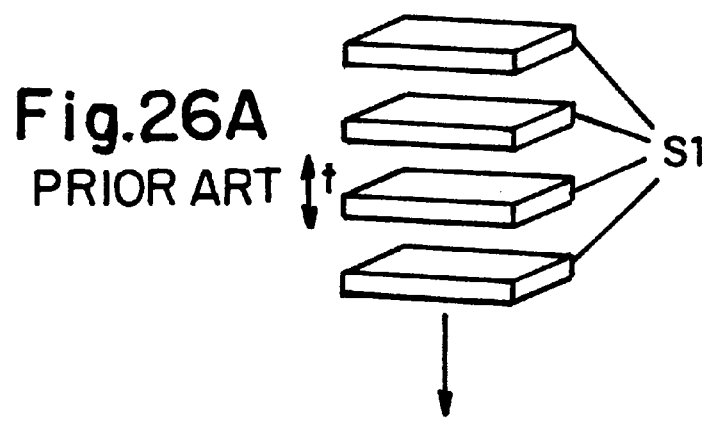
Figure 26B:
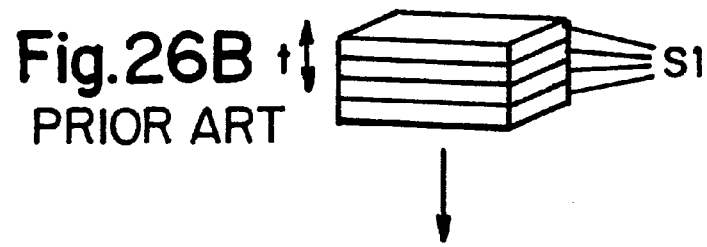
Figure 26C:
Figure 26D:
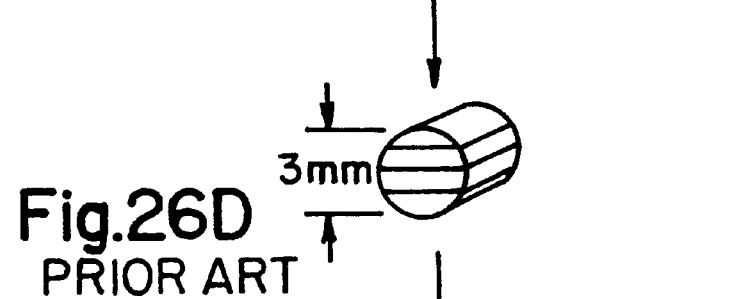
Figure 26E:
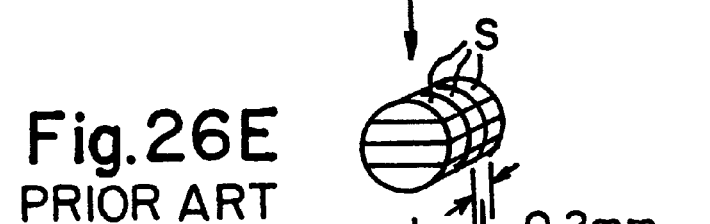
Figure 26F:
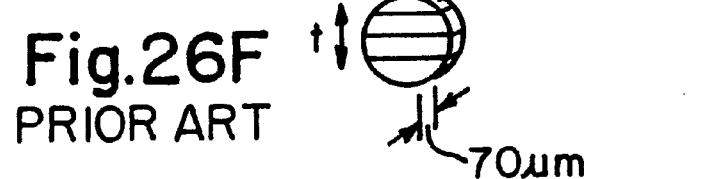
Figure 27A:
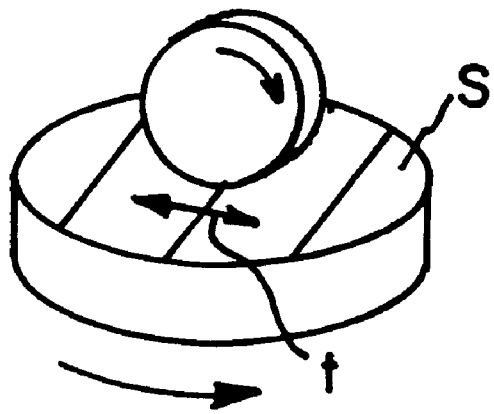
Figure 27B:
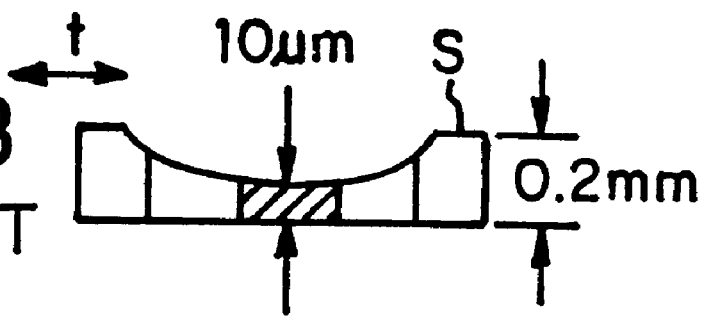
Figure 27C:
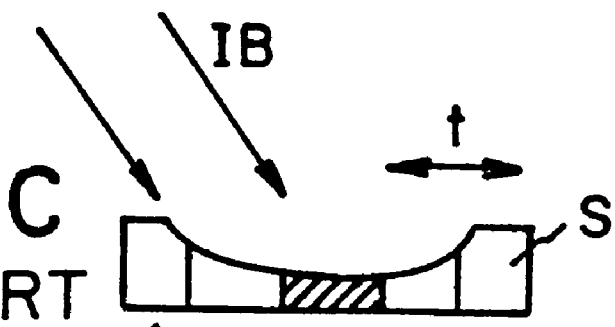
Figure 27D:
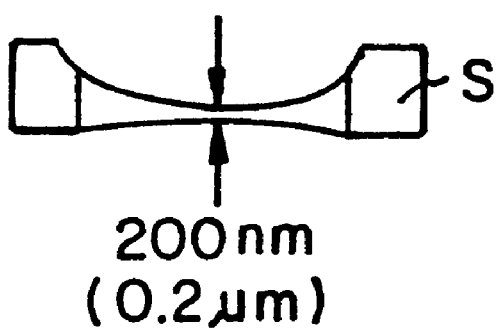

The operation of the specimen preparation apparatus constructed in this way is next described. The insert of FIG. 2 is an enlarged view of the specimen S. This corresponds to the aforementioned rodlike specimen S1 cut out from the silicon wafer W (FIG. 25). The processed surface SA of the specimen S is a side surface extending longitudinally. This side surface measures 0.1 mm×3 mm. The thickness of the specimen S is 0.3 mm.

That is, the shorter dimension 0.1 mm of the processed surface SA of the specimen is prepared smaller than the diameter 1 mm of the ion beam IB for etching the specimen. In other words, the diameter of the ion beam IB is large enough to simultaneously etch the whole shorter dimension of the processed surface SA.

The operator first mounts the specimen to the specimen stage 13 and then operates the vacuum pump 3. Subsequently, he brings the mirror 15 from the position indicated by the solid line in FIG. 1 into the position indicated by the broken line, i.e., into the optic axis of the ion beam generator. If the mirror 15 is placed on the optic axis of the ion beam generator, the TV camera 10 sees the processed surface SA of the specimen S across the beam-blocking member 22. The obtained image is displayed on the display device 117. The operator adjusts the micrometer so as to move the beam-blocking member 22 along the Y-axis while watching this image in such a way that a region of interest on the specimen is hidden behind the linear beam-blocking member 22, i.e., beam-blocking member 22 is brought into the region of interest. After the adjustment of the position in the Y-direction is completed in this manner, the operator moves the mirror 15 off the optic axis. Then, he moves the elevatable table 4 upward while watching the image displayed on the display device 116 such that the space between the beam-blocking member 22 and the processed surface SA becomes less than 10 μm.

When the adjustment of the beam-blocking member 22 and the adjustment of the height of the specimen are completed in this way, an ion beam is emitted from the ion beam generator 17 and made to impinge on the specimen. Thus, the first stage of etching is started. As shown in FIG. 3A, the irradiated region SA2 of the processed surface SA of the specimen is etched. The beam-blocking member 22 prevents the nonirradiated region SA1 from being etched. After the specimen has been etched to a desired depth, for example several micrometers, the irradiation of the ion beam IB is stopped. At this time, the surface of the irradiated region SA2 has lowered to level SB (FIG. 3A) as a result of the etching.

If the first stage of etching of the specimen is completed in this way, the operator again moves the mirror 15 onto the optic axis. He then adjusts the micrometer 24 so as to move the beam-blocking member 22 to the right (i.e., in the direction opposite to the Y-axis), as shown in FIG. 3C, while watching the image presented on the display device 117. That is, he moves the linear beam-blocking member 22 until it becomes vertical to the right end fringe of the nonirradiated region SA1 which is a boundary line between the nonirradiated region SA1 and the irradiated region SA2.

After the position of the linear beam-blocking member 22 is adjusted in this way, the ion beam generator 17 again emits the ion beam toward the specimen, thus initiating the second stage of etching. As shown in FIG. 3C, of the nonirradiated region SA1, a region SA12 which is now irradiated with the ion beam is etched. Of the irradiated region SB, a region SB2 which is also irradiated with the ion beam is also etched. The linear beam-blocking member 22 prevents a presently nonirradiated region SA11 of the nonirradiated region SA1 and a presently nonirradiated region SB1 of the irradiated region SB from being etched. When the specimen is etched to a given depth (e.g., several micrometers or more), the irradiation of the ion beam IB is stopped. As a result, the surfaces of the irradiated regions SA12 and SB2 are lowered to level SC in FIG. 3C, and a protruded portion Sa less than 200 nm thick is produced. FIG. 3D is a perspective view of the specimen prepared by the processing steps as described thus far, the specimen being for use in electron microscopy. The thin protruded portion Sa is observed with the electron microscope.

While one embodiment of the present invention has been described thus far, a case where a specimen is prepared by the use of the turntable 12 of the specimen preparation apparatus shown in FIG. 2 is next described by referring to FIGS. 4A–4D, 5A–5D.

As shown in FIGS. 4A–4C, the ion beam IB is made to impinge on the specimen while the linear beam-blocking member 22 is placed close to the processed surface SA of the specimen. The irradiated portion is etched, so that the specimen S has a protruded portion Sa as shown in FIG. 4D.

When the linear beam-blocking member 22 is translated similar to the method described already in connection with FIGS. 3A–3D to perform the second stage of etching, the protruded portion Sa becomes a thin film, which can be observed with the electron microscope. In this case, however, both ends of the thin protruded portion of the specimen S are connected to the thick portion of the specimen. Thus, a stress is applied across the thin film portion, resulting in flexure. This may make the specimen unsuitable for electron microscopy.

Figure 5A:
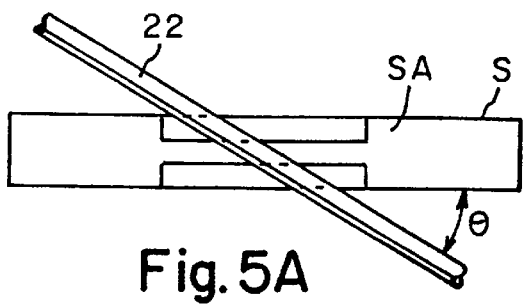
FIGS. 5A–5D, 6, 7A, 7B, 8A–8C are views illustrating etching of specimens.
Figure 5B:
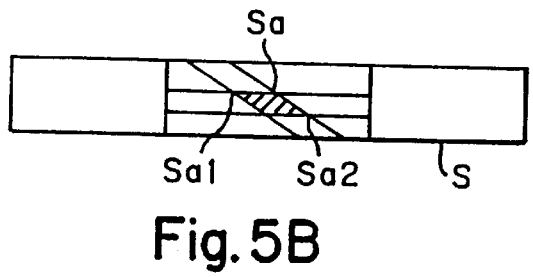
Figure 5C:
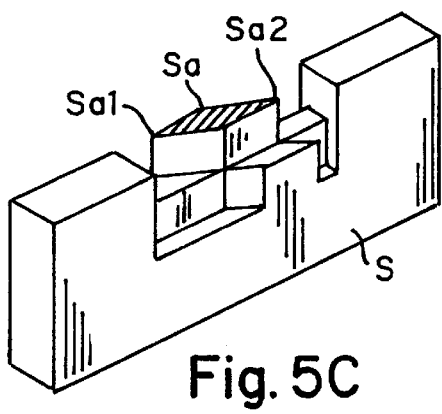

Therefore, the second etching is carried out in the manner described now. First, as shown in FIG. 5A, a relative rotation is produced between the beam-blocking member 22 and the specimen S. For example, the turntable 12 is rotated by the rotating means (not shown) so that the specimen S rotates through an angle of θ relative to the beam-blocking member 22, as shown in FIG. 5A. Under this condition, the ion beam is caused to hit the specimen. As shown in FIG. 5B, a hatched rhomboidal portion Sa is not etched but remains protruded. That is, the thin protruded portion Sa of rhomboidal cross section is left behind. FIG. 5C is a perspective view of the specimen S under this condition. Both ends Sa1 and Sa2 of the protruded portion Sa of the rhomboidal cross section are very thin and can be observed with the electron microscope.

Where the region capable of being observed with the microscope is 2 mm, it is necessary to set the distance between both ends Sa1 and Sa2 less than 2 mm. Accordingly, where the distance L0 shown in FIG. 5D is set to about 1 mm and the thickness of the specimen capable of being penetrated by the electron microscope is 200 nm, the observable region of the protruded portion Sa of the specimen S has the following dimensions.

Figure 5D:
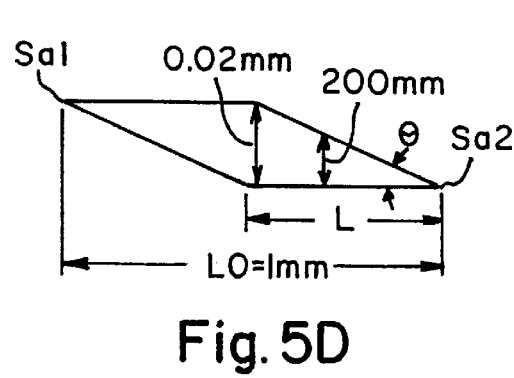

In FIG. 5D, since the angle θ is small, θ=0.02 mm/0.5 mm=0.04. Letting L be the length of the region having thicknesses less than 200 nm, we have $$Lθ=200 \text{ nm}$$

That is, $$L=200 \text{ nm}/θ=200 \text{ nm}/0.04=5000 \text{ nm}=5 \text{ μm}$$

Thus, the length L of the observable region shown in FIG. 5D is 5 μm. Where the observation is made by an electron microscope with a magnification of 100,000×, we have 5 μm×100,000=500 mm=50 cm Hence, a region which can be sufficiently observed is obtained.

Figure 6:
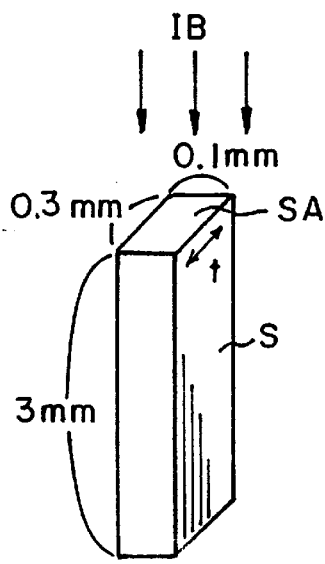

As shown in FIG. 6, the specimen S can be mounted to the specimen stage 13 in such a way that a smaller surface of the specimen S having dimensions 0.3 mm×0.1 mm is the processed surface SA.

Figure 7A:
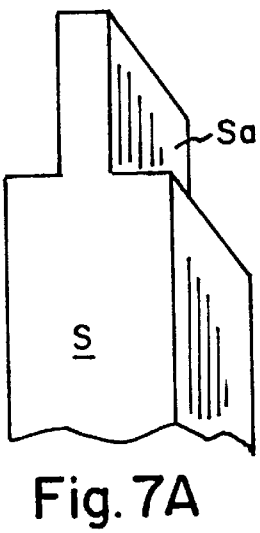
Figure 7B:
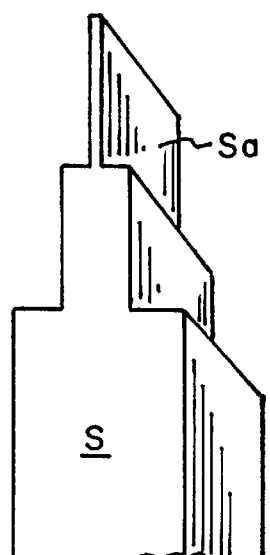

In this case, if the first stage of etching, movement of the beam-blocking member, and second stage of etching are carried out in the same way as in the method described previously in connection with FIGS. 3A–3D, the first etching process results in etching of the specimen, as shown in FIG. 7A. The second etching process produces a protruded portion Sa less than 200 nm thick, as shown in FIG. 7B.

Figure 8A:
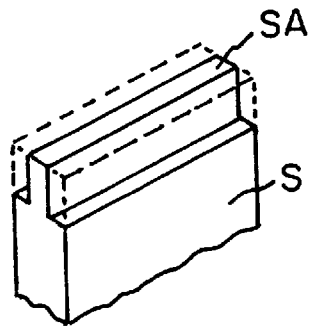
Figure 8B:
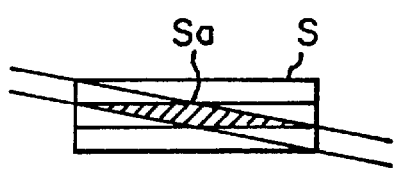
Figure 8C:
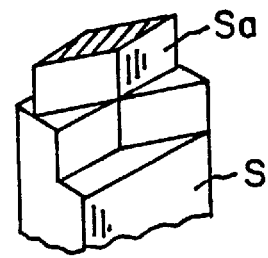

FIGS. 8A, 8B, and 8C show an example where the surface measuring 0.3 mm×0.1 mm (FIG. 6) is to be processed by the procedure described already in connection with FIGS. 4A–4D, 5A–5D. It is observed that the protruded portion Sa is formed on the end surface of the specimen, or the side surface measuring 0.1 mm×0.3 mm.

Figure 9:
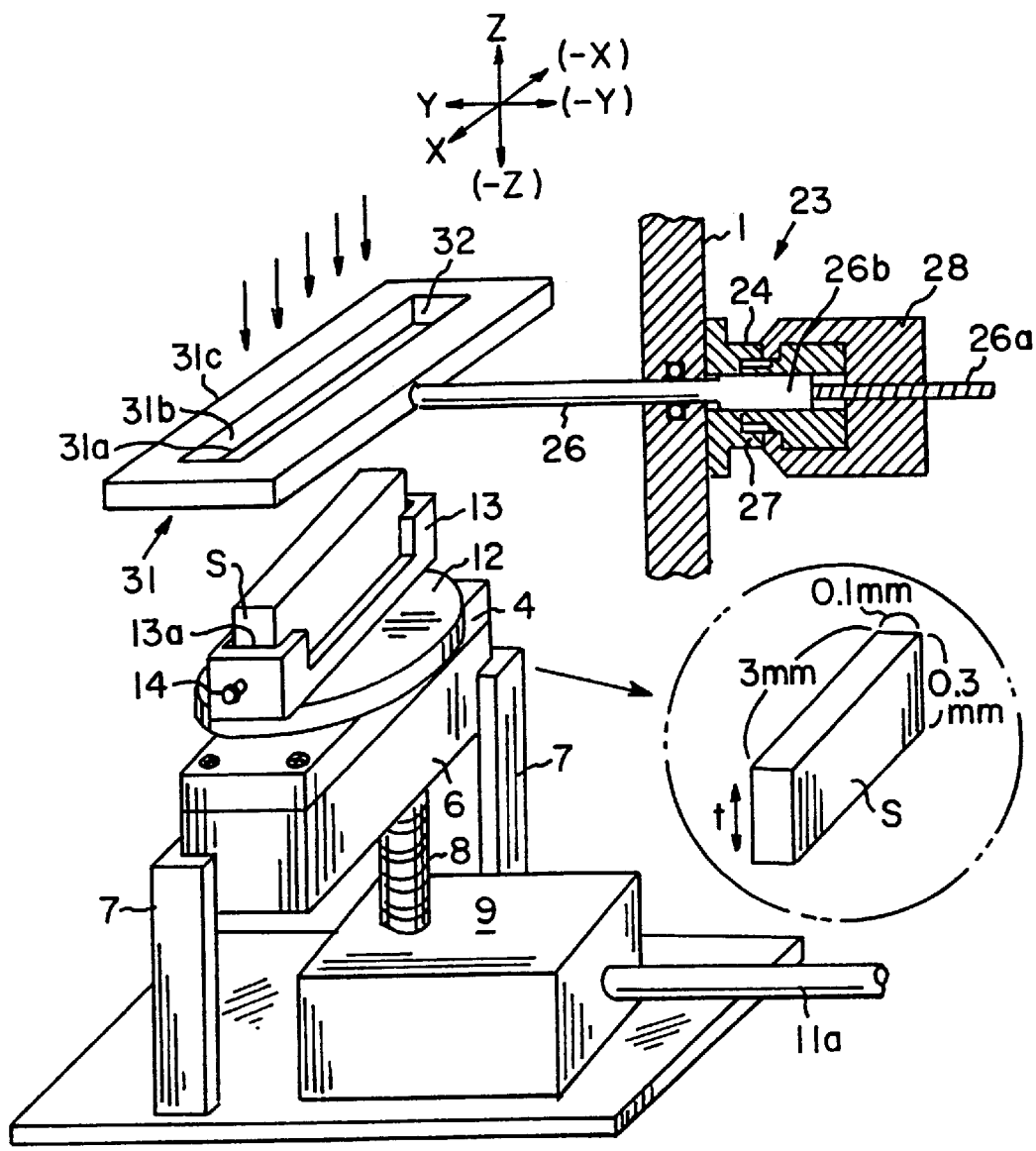
FIG. 9 is a perspective view similar to FIG. 2, but showing other beam-blocking member and specimen stage forming main components of another specimen preparation apparatus according to the invention.

Another specimen preparation apparatus for electron microscope according to the invention is next described by referring to FIGS. 9, 10A–10C, 11A–11C. FIG. 9 is an enlarged view of a support device and a specimen stage 13. The support device holds a beam-blocking member which is a main component of this specimen preparation apparatus. FIGS. 10A–10C illustrate the operation of the specimen preparation apparatus when it is used in one manner. FIGS. 11A–11C illustrate the operation of the apparatus when it is used in a different manner. It is to be noted that like components are indicated by like reference numerals in various figures and that those components which have been already described will not be described in detail below.

This embodiment is similar to the embodiment described in conjunction with FIGS. 1 and 2 except for the following points. Instead of the linear beam-blocking member 22 and the support arm 29 holding this blocking member 22, a beam-blocking plate 31 placed within a plane perpendicular to the ion beam IB is used. This beam-blocking plate 31 is provided with a rectangular opening 32 and has parallel side fringes 31a, 31b, 31c extending along the longer sides of a processed surface SA of the specimen S. The length of the opening 32 taken along the Y-axis is about 2 mm. The length taken along the X-axis is about 10 mm.

As shown in FIG. 10A, the ion beam generator 17 emits the ion beam IB while the beam-blocking plate 31 is adjacent to the processed surface Sa of the specimen to perform the first etching step. Because of the side fringe 31a of the beam-blocking plate 31, one nonirradiated region SA1 and one irradiated region SA2 are formed in the processed surface SA. The surface of the irradiated region SA2 is etched, thus giving rise to a surface SB shown in FIG. 10A.

The beam-blocking plate 31 is moved to the right, or in the Y-direction, by the micrometer 24, as shown in FIG. 10B. That is, the beam-blocking plate 31 is moved until it becomes vertical to the left side fringe of the nonirradiated region SA1 (i.e., the boundary line between the nonirradiated region SA1 and the irradiated region SA2) Then, the side fringe 31b is so arranged that a narrow region SA11 in the nonirradiated region SA1 is not irradiated with the beam during the second etching step, the narrow region SA11 extending along the boundary line with the irradiated region SA2. Under this condition shown in FIG. 10B, the surface of the specimen is divided into the nonirradiated region SA11 and an irradiated region SA12. The surface SB shown in FIG. 10A is not irradiated during the second etching step shown in FIG. 10B.

Under the state shown in FIG. 10B, the ion beam IB is irradiated to carry out the second etching step. The irradiated region SA12 which is currently being irradiated with the beam is etched to form the level SC indicated by the solid line in FIG. 10B. The region SA11 (FIG. 10B) which is irradiated neither during the first etching step nor during the second etching step is left as a thin protruded portion Sa having a thickness of 200 nm or less. As a result, a rodlike specimen S having the thin protruded portion Sa on its longitudinal end surface is prepared, the specimen S being adapted for electron microscopy. The thin protruded portion Sa can be observed with the electron microscope.

The operation of the specimen preparation apparatus shown in FIG. 9 when it is used in a different manner is next described by referring to FIGS. 11A–11C. First, during the first etching step, the side fringe 31b of the beam-blocking plate 31 is placed over the specimen, as shown in FIG. 11A. Under this condition, the ion beam is made to impinge on the specimen. During the second etching step, the side fringe 31c of the beam-blocking plate 31 is positioned over the specimen, as shown in FIG. 11B. In this state, the ion beam is made to hit the specimen. As a result of this etching, the nonirradiated region SA11 is left as the thin protruded portion Sa less than 200 nm thick. FIG. 11C is a perspective view of the specimen prepared in this way. The thin protruded portion Sa is observed by the electron microscope.

Obviously, even with the specimen preparation apparatus using the beam-blocking plate as shown in FIG. 9, the specimen surface measuring 0.3 mm×0.1 mm can be processed by making the specimen stationary as shown in FIG. 6 in preparing the specimen.

Figure 12:
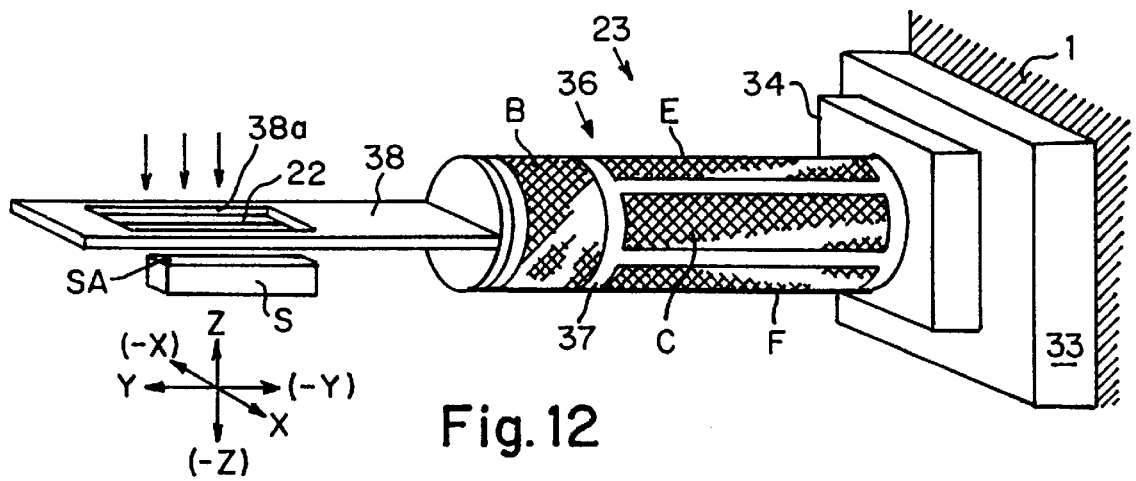
FIG. 12 is an enlarged perspective view of a beam-blocking member support device that is a main component of a further specimen preparation apparatus according to the invention.
Figure 13A:
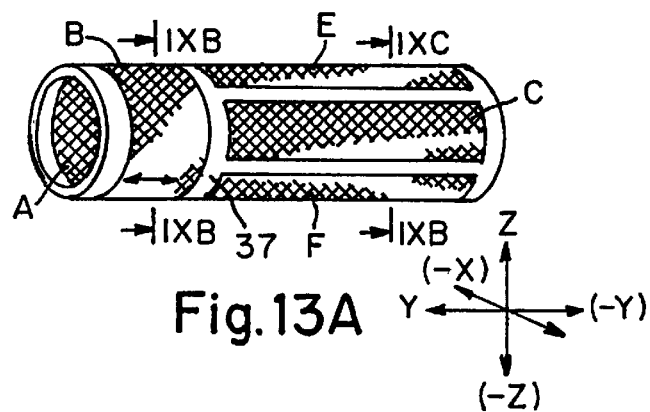
FIGS. 13A–13C are diagrams particularly showing a cylindrical piezoelectric XYZ actuator forming the beam-blocking member support device shown in FIG. 12.
Figure 13B:
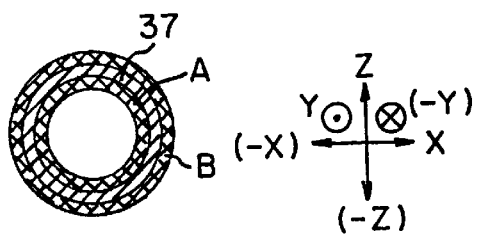
Figure 13C:
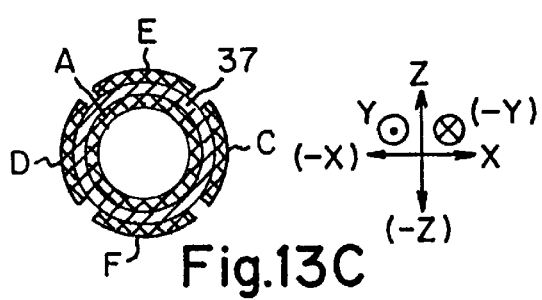
Figure 14:
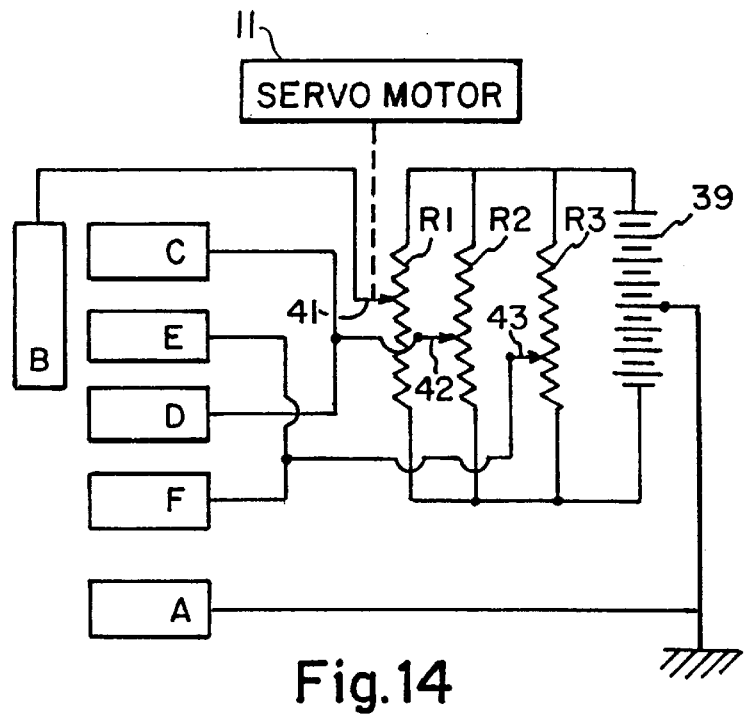
FIG. 14 is a circuit diagram of a circuit for driving the cylindrical piezoelectric XYZ actuator shown in FIGS. 13A–13C.
Figure 16A:
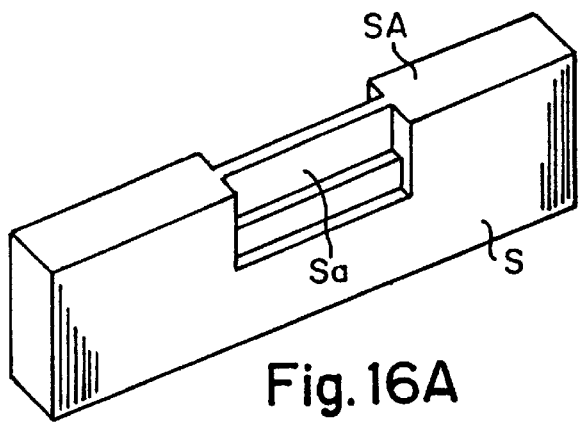
FIGS. 16A–16B are perspective views of a specimen prepared in accordance with the invention.
Figure 16B:
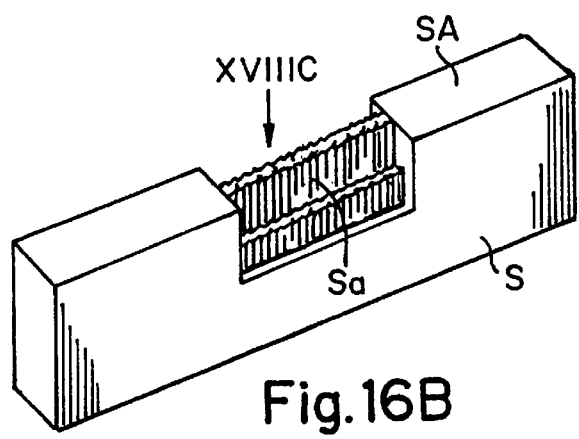
Figure 16C:
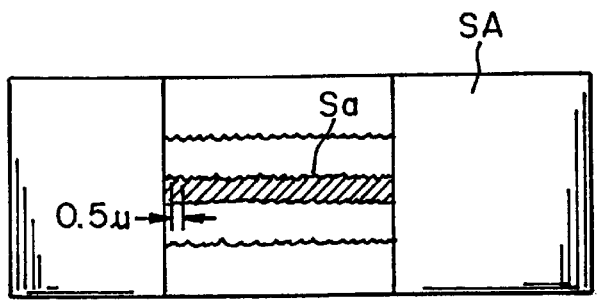
FIG. 16C is a top view of the prepared specimen shown in FIGS. 16A–16B.
Figure 17A:
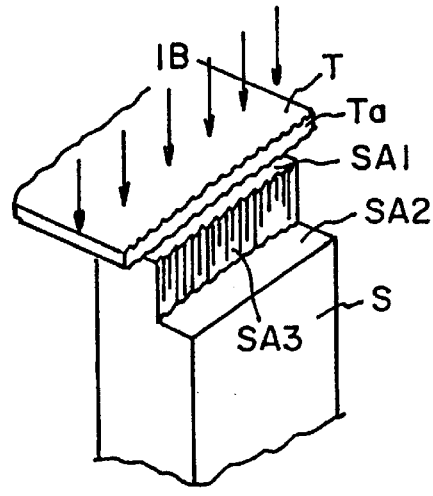
FIGS. 17A–17B are diagrams illustrating the manner in which a specimen is etched.
Figure 17B:
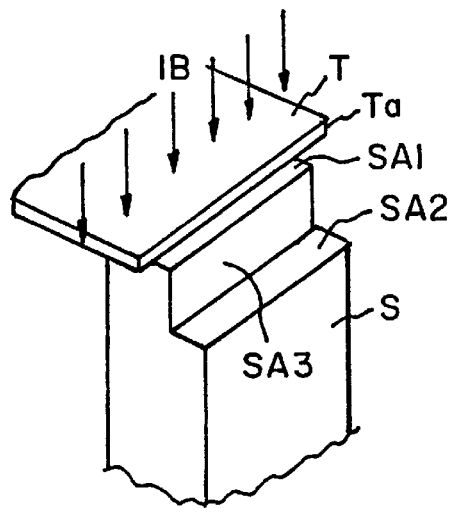

A further specimen preparation apparatus according to the invention is next described by referring to FIGS. 12, 13A–13C, 14, 15A–15E, 16A–16C, and 17A–17B. FIG. 12 is an enlarged view of a beam-blocking member support device forming a main component of this specimen preparation apparatus FIGS. 13A–13C particularly show a cylindrical piezoelectric XYZ actuator forming the beam-blocking member support device shown in FIG. 12. FIG. 14 shows a circuit for driving the cylindrical piezoelectric XYZ actuator shown in FIGS. 13A–13C. FIGS. 15A–15E are diagrams illustrating the operation of the device shown in FIG. 12. FIG. 16A is a perspective view of a specimen prepared by the present embodiment. FIG. 16B shows a specimen prepared, not using the technique of the present embodiment. FIG. 16C is a plane view taken in the direction indicated by the arrow XVIIIC of FIG. 16B. FIGS. 17A–17B are diagrams illustrating the reason why the construction of the present embodiment is adopted. FIG. 17A illustrates an etching step where the configuration of the present embodiment is not used. FIG. 17B illustrates an etching step where the present embodiment is implemented.

In FIG. 17A, a side surface Ta of a beam-blocking member T that blocks the ion beam IB has microscopic irregularities such as crystal grains. The ion beam IB travels along this uneven side surface and collides against the processed surface SA of the specimen S. Irregularities are created at the boundary line between the nonirradiated region SA1 and the irradiated region SA2. Therefore, stripes of irregularities are created on the etched side surface SA3 of the specimen S. Where the beam-blocking member T is made of tungsten, the stripes are formed at intervals of about 0.5 μm. The interval is determined according to the material of the beam-blocking material T.

The side surface SA3 is a surface to be observed by the electron microscope. The stripes of irregularities are undesirable. We have discovered that the stripes of irregularities can be prevented, as shown in FIG. 17B, by performing etching while producing relative-vibrations between the specimen S and the beam-blocking member T along the side surface Ta of the blocking member T which blocks the beam. The configuration of the present invention has been made, based on this finding.

The present embodiment is similar to the configuration shown in FIGS. 1 and 2 except that the beam-blocking member support device 23 holding the linear beam-blocking member 22 differs from the support device of the previous embodiment in structure.

Referring to FIG. 12, the beam-blocking member support device 23 of this embodiment has a base member 33 firmly mounted to the inner side surface of the chamber 1 An actuator-holding plate 34 is mounted to the inner surface of the base member 33. A cylindrical piezoelectric XYZ actuator 36 for producing a relative movement between the specimen and the beam-blocking member is held to the actuator-holding plate 34. The actuator 36 has a cylindrical member 37 made of a piezoelectric substance. This cylindrical member 37 is so placed that its axis extends horizontally. The right end of the cylindrical member 37 forms a reference plane and is attached to the actuator-holding plate 34. The left end of the cylindrical member 37 which forms a driving surface is a free end.

A cylindrical electrode A which is grounded is formed substantially over the whole cylindrical inner surface of the cylindrical member 37. A cylindrical electrode B is formed at the left end of the outer surface of the cylindrical member 37. The left end, or the driving surface, of the cylindrical member 37 can be driven in the Y-direction by applying a positive or negative voltage to the electrode B.

A pair of X-motion electrodes, C and D, is formed on the outer surface of the cylindrical member 37 at the right of the electrode B. The electrodes C and D are spaced from each other along the X-axis. The left end of the cylindrical member 37 can be driven in the X-direction by applying a positive or negative voltage to the X-motion electrodes C and D.

A pair of Z-motion electrodes, E and F, is formed on the outer surface of the cylindrical member 37 to the right of the electrode B. These electrodes E and F are spaced from each other along the Z-axis. The left end, or the driving surface, of the cylindrical member 37 can be driven vertically, or in the Z-direction, by applying a positive or negative voltage to the Z-motion electrodes E and F.

The cylindrical member 37 made of the piezoelectric substance and the cylindrical piezoelectric XYZ actuator 36 consisting of the electrodes A–F cooperate to form a relative movement-producing device for moving the linear beam-blocking member 22 relative to the specimen S.

A blocking member support arm 38 extending to the left, or in the Y-direction, is mounted to the left end, or driving surface, of the cylindrical member 37. An opening 38a is formed at the left end of the blocking member support arm 38. This linear beam-blocking member 22 extending horizontally, or in the Y-direction, is held under the opening 38a.

Referring to FIG. 14, a dc power supply 39 and arcuate variable resistors R1–R3 are connected in parallel. The resistors R1–R3 are used for Y-motion, X-motion, and Z-motion, respectively. The power supply 39 has a tapping at which the voltage is halved The electrode A and the tapping are grounded, as mentioned above. The electrode B is connected with a Y-motion connector terminal 41 for moving the left end, or driving surface, of the cylindrical member 37 in the Y-direction. The connector terminal 41 is rotated while its front end is kept in contact with the arcuate, Y-motion resistor R1. The connector terminal 41 is driven by a servomotor M.

The cylindrical piezoelectric XYZ actuator 36 shows a characteristic 0.4 $\mu$m/V for X- and Z-motions and a characteristic 0.04 $\mu$m/V for Y-motion. Hence, fine position adjustments can be sufficiently made.

Accordingly, in order to periodically produce a potential corresponding to half of the interval of the stripes of irregularities on the side surface of the linear beam-blocking member 22, i.e., to cause the left end, or driving surface, of the cylindrical member 37 to move 0.4 $\mu$m, a periodic voltage change (e.g., a preset voltage plus minus 5 V) is given to the servomotor M. A well-known voltage controller may be used to cause the left end of the cylindrical member 37 to move 0.4 $\mu$m.

The electrodes C and D are connected with an X-motion connector terminal 42 which acts to move the left end, or driving surface, of the cylindrical member 37 in the X-direction. The X-motion connector terminal 42 is rotated while its front end is kept in contact with the arcuate X-motion resistor R2. The X-motion connector terminal 42 is manually driven.

The electrodes E and F are connected with a Z-motion connector terminal 43 for moving the left end, or driving surface, of the cylindrical member 37 in the Z-direction. This Z-motion connector terminal 43 is similar to the X-motion connector terminal 42 in structure and driven manually.

The operation of this embodiment constructed in this way is now described. Also in this embodiment, the shorter dimension of the dimensions 0.1 mm×3 mm of the processed surface of the specimen is set smaller than the diameter 1 mm of the ion beam IB used for etching the specimen. The specimen S is mounted to the specimen stage 13, and the processed surface SA of the specimen S is moved upward until it comes close to the linear beam-blocking member 22, in the same way as in FIGS. 1 and 2. The position of the linear beam-blocking member 22 in the X-direction is adjusted by adjusting the voltage applied to the electrodes C and D of the cylindrical piezoelectric XYZ actuator 36 while the processed surface Sa of the specimen is kept close to the blocking member 22. This adjustment is made while watching the display device 117. Then, the voltage applied to the electrodes E and F is adjusted to adjust the vertical position of the linear beam-blocking member 22. This adjustment is also made while watching the display device 116.

Figure 15A:
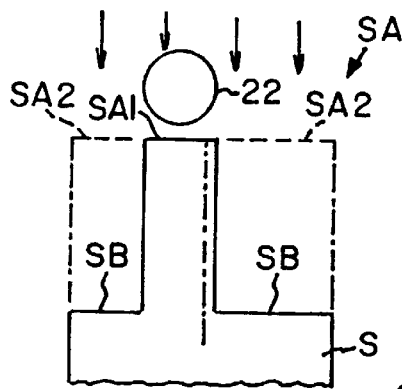
FIGS. 15A–15D are diagrams illustrating the operation of the device shown in FIG. 12.
Figure 15B:
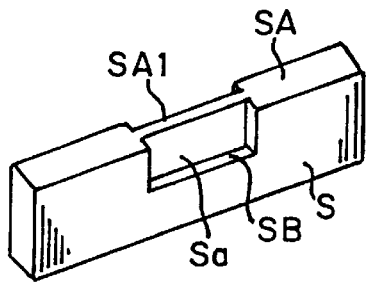

After these adjustments are completed, the ion beam generator 17 emits the ion beam IB to etch the specimen, as shown in FIG. 15A. For this purpose, a voltage is applied to the electrode B of the cylindrical piezoelectric XYZ actuator 36 to vibrate the linear beam-blocking member 22 in the Y-direction, the blocking member extending in the Y-direction. Preferably, the amplitude of the vibrations is an integral multiple of half of the size of crystal grains lying in the Y-direction on the side surface of the blocking member 22. This will be described in detail later.

In FIG. 15A, the linear beam-blocking member 22 produces linear nonirradiated region SA1 and irradiated regions SA2 on the both sides of the nonirradiated region SA1 on the processed surfaces SA of the specimen. The surfaces of the irradiated regions SA2 are etched to level SB shown in FIG. 15A.

Figure 15D:
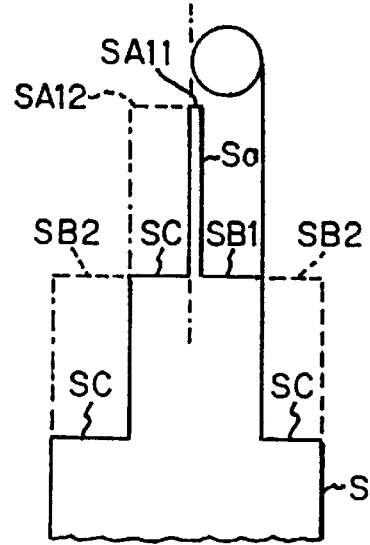
Figure 15C:
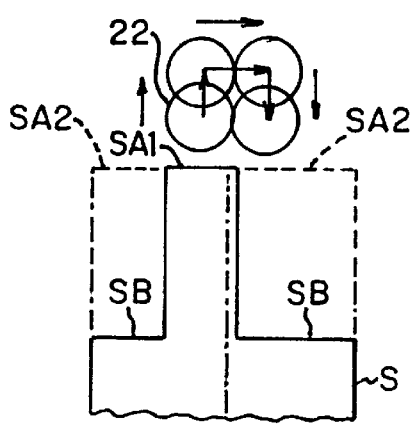

Then, as shown in FIG. 15C, the cylindrical piezoelectric XYZ actuator 36 is operated to move the linear beam-blocking member 22 upward, or in the Z-direction and then in the X-direction. Thereafter, the blocking member 22 is moved downward to obtain a state as shown in FIG. 15D. The blocking member 22 is moved in the X-direction after raised, for the following reason. Since the blocking member 22 is very close to the processed surface of the specimen, the blocking member 22 must be prevented from touching the processed surface when the blocking member 22 is moving in the X-direction.

Referring to FIG. 15D, the linear beam-blocking member 22 is so located that the narrow region SA11 of the nonirradiated region SA1 extending along the boundary line with the irradiated region SA2 is not irradiated during the next second etching step. Under this condition, the nonirradiated region SA1 shown in FIG. 15C is divided into the nonirradiated region SA11 and irradiated region SA12 during the second etching step. The surface SB shown in FIG. 15C is divided into the nonirradiated region SB1 and irradiated region SB2.

Under the condition indicated by the phantom line in FIG. 15D, the ion beam IB is emitted to perform the second etching step. The linear beam-blocking member 22 is vibrated in the Y-direction in the same way as in the first etching step.

As a result of this second etching step, the irradiated regions SA12 and SB2 are etched to the level SC indicated by the solid line in FIG. 15D. The region SA11 which was irradiated neither during the first etching step nor during the second step is left as a protruded portion Sa less than 200 nm thick. As shown in FIG. 16A, a rodlike specimen S having the thin protruded portion Sa on its longitudinal side surface is prepared, the specimen S being adapted for electron microscopy. The thin protruded portion Sa can be observed with the electron microscope.

FIG. 16A is a perspective view of a specimen S obtained when the first and second etching steps are performed while vibrating the linear beam-blocking member 22 of the present embodiment in its longitudinal direction. FIG. 16B is a perspective view of a specimen S derived when the blocking member is not vibrated. FIG. 16C is a plan view taken in the direction indicated by the arrow XVIII of FIG. 16B. In FIGS. 16B and 16C, stripes of irregularities are created on the thin protruded portion Sa left after the first and second etching steps.

As can be seen from the descriptions of FIGS. 16A–16C, formation of the stripes of irregularities on the thin protruded portion Sa formed on the specimen S can be prevented by vibrating the blocking member 22 in its longitudinal direction. In the present embodiment, the linear beam-blocking member 22 is vibrated. It is also possible to vibrate the specimen stage 13.

Figure 18:
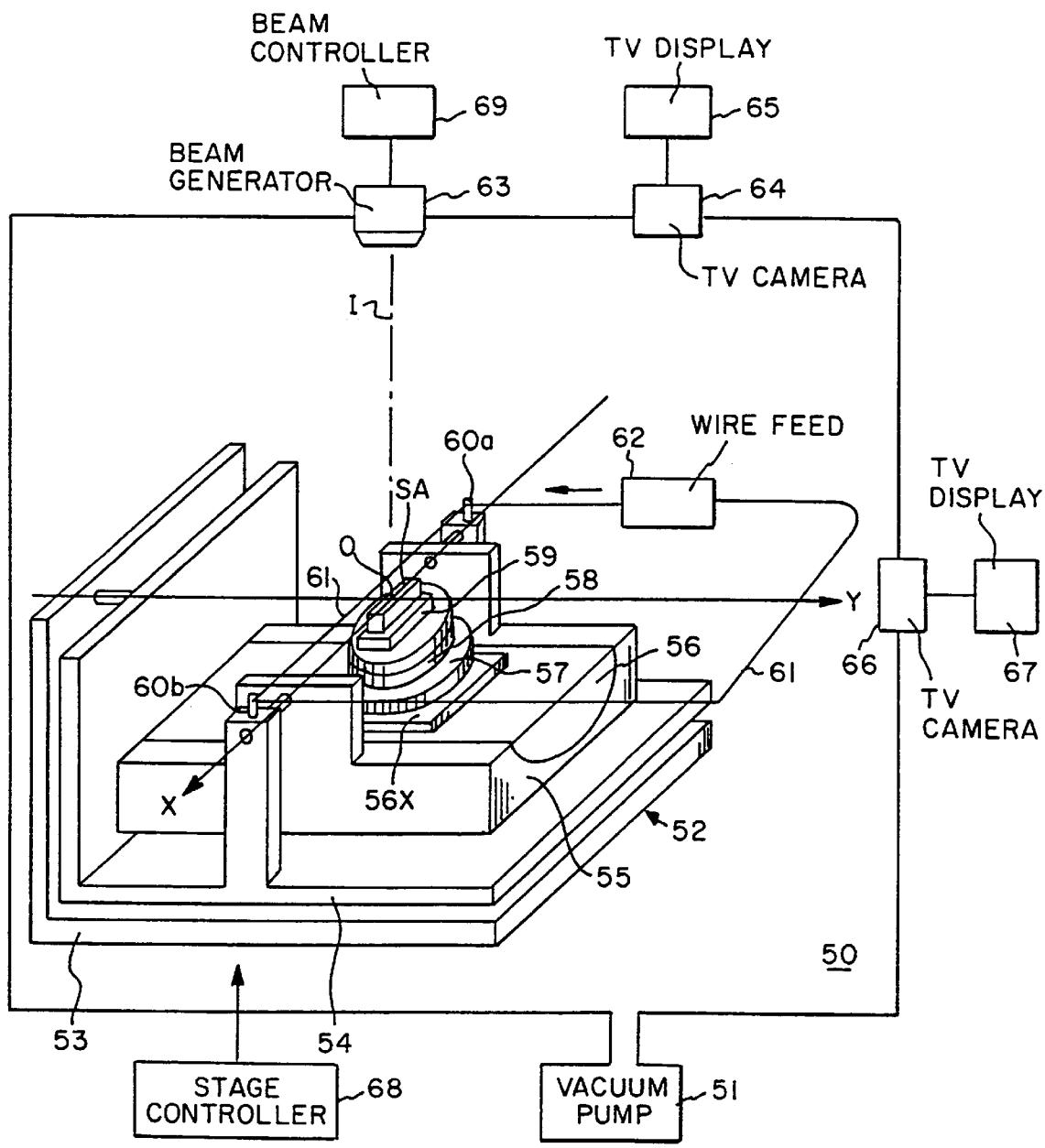
FIG. 18 is a perspective view of a yet other specimen preparation apparatus according to the invention.

Referring next to FIG. 18, there is shown a still other specimen preparation apparatus according to the present invention. A vacuum pump 51 is connected with a specimen-processing chamber 50. A specimen stage 52 is positioned inside the processing chamber 50. This specimen stage 52 comprises a Y2-motion stage 53 capable of moving in the Y-direction, a Y-tilt stage 54 placed on the Y2-motion stage 53 and capable of tilting about the Y-axis, an X-tilt stage 55 placed on the Y-tilt stage 54, a Y1-motion/tilt stage 56 placed on the X-tilt stage 55, an X-motion stage 56X placed on the Y1-motion/tilt stage 56, a turntable 57 placed on the X-motion stage 56X, and a Z-motion stage 58 placed on the turntable 57 and capable of moving in the direction of rotation of the turntable 57. When the Y-tilt stage 54 is not tilted, the X-tilt stage 55 tilts about the X-axis. When neither the Y-tilt stage 54 nor the X-tilt stage 55 is tilted, the Y1-motion/tilt stage 56 is capable of moving in the Y-direction and of tilting about the Y-axis. When neither the Y-tilt stage 54 nor the Y1-motion/tilt stage is tilted, the X-motion stage 56X can move in the X-direction. The turntable 57 is able to rotate about an axis perpendicular to the plane on which the turntable 57 is placed. A specimen holder 59 holding the specimen S is withdrawably attached to the Z-motion stage 58. Since the position of the specimen is so adjusted that the processed surface SA of the specimen S lies at the intersection O of the X- and Y-axes, the processed surface SA is kept at the intersection O if any of the Y-tilt stage 54, X-tilt stage 55, and Y1-motion/tilt stage 56 is tilted.

Figure 19A:
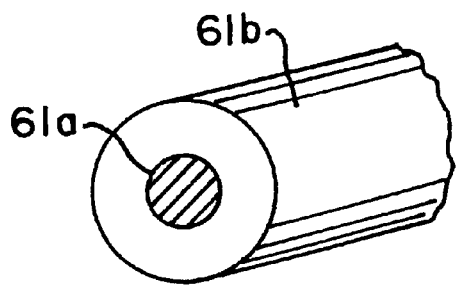
FIGS. 19–21 are views illustrating the operation of the apparatus shown in FIG. 18.
Figure 19B:
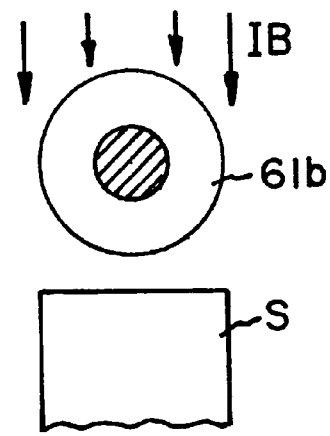
Figure 19C:
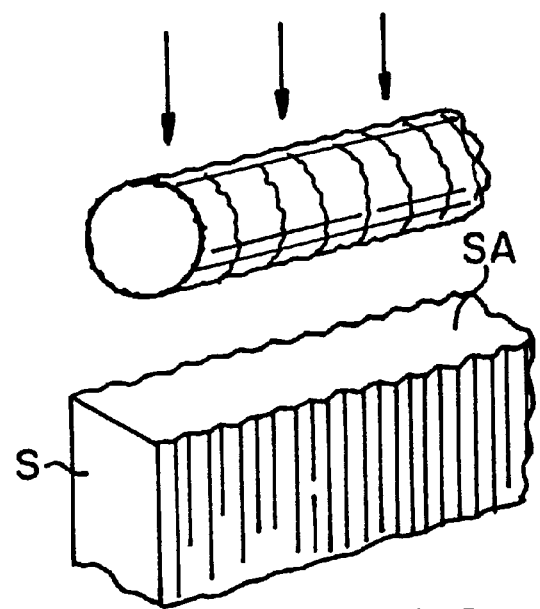

Wire support members 60a and 60b are fixedly mounted on the Y-tilt stage 54. An ion beam-blocking wire 61 is stretched between the wire support members 60a and 60b. As shown in FIG. 19(A), this wire 61 comprises a tungsten wire 61a enclosed in an amorphous metal layer 61b. For instance, this amorphous metal layer is a nickel-phosphorus electroless plating. Since the irradiated portion of the ion beam-blocking wire 61 is not crystallized but rather is made from an amorphous metal in this way, if the ion beam hits the amorphous metal 61b, the surface is etched but not made uneven, as shown in FIG. 19(B) Consequently, the etched surface of the specimen is smooth, as shown in FIG. 19(B) If the irradiated portion of the ion beam-blocking wire is made from crystalline metal, then the surface is etched crystal by crystal due to the ion beam irradiation. Hence, the surface becomes uneven, as shown in FIG. 19(C). Since the surface of the etched specimen becomes uneven as shown in FIG. 19(C), it is important that the irradiated portion of the ion beam-blocking wire be made from amorphous metal. In the present embodiment, when a wire-feeding portion 62 is operated, the ion beam-blocking wire 61 is moved in the direction indicated by the arrow. Therefore, if the wire is made too thin, the wire is fed so that a fresh portion not yet irradiated is subjected to the ion beam.

A tiltable ion beam generator 63 is mounted at the top of the processing chamber 50. The tilt axis of the ion beam generator 63 is coincident with the X-axis in order that the position on the specimen hit by the ion beam be not varied when the ion beam generator 63 is tilted. A TV camera 64 is mounted at the top of the processing chamber 50 at a distance from the ion beam generator 63 along the Y-axis. A display device 65 is connected with this TV camera 64 so that an image picked up by the TV camera 64 is displayed on the display device 65. Another TV camera 66 is disposed at a side of the processing chamber 50. An image picked up by the TV camera 66 is presented on a display device 67. A stage controller 68 controls the specimen stage 52. An ion beam controller 69 controls the ion beam generator 63.

The configuration of the apparatus shown in FIG. 18 has been described The operation is next described The specimen holder is mounted on the Z-motion stage 58 via a specimen exchange mechanism (not shown).

In this construction, if the interior of the processing chamber 50 is evacuated by the vacuum pump 51, the operator first operates the stage controller 68 to move the Y2-motion stage 53 in such a way that the ion beam-blocking wire 61 and the specimen S are brought immediately under the TV camera 64, i.e., the wire 61 is displayed at the center of the screen of the display device 65. Then, he operates the stage controller 68 to rotate the Y1-motion/tilt stage 56 while watching the display device 67 in such a way that the processed surface SA of the specimen is made parallel to the ion beam-blocking wire 61. He also operates the stage controller 68 to move the Z-motion stage 58 so that the distance between the processed surface SA and the wire 61 decreases below 10 μm while watching the display device 67. Following the movement of the Z-motion stage 58, the processed surface SA is located at the intersection O described above. Then, the operator, while watching the display device 65, operates the stage controller 68 to move the X-motion stage 56X in the X-direction, move the Y1-motion/tilt stage 56 in the Y-direction, or tilt the turntable 57 in such a way that a specimen region of interest is brought below the ion beam-blocking wire 61.

Figure 20A:
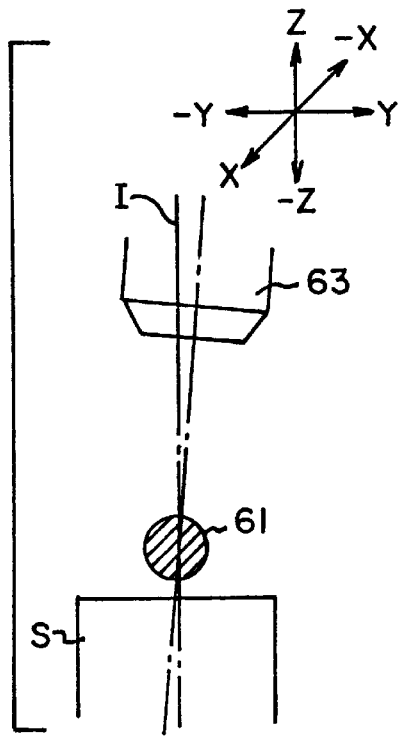
Figure 20B:
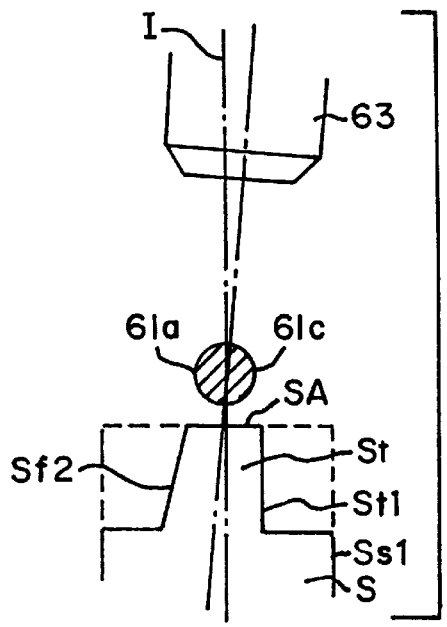

If the position at which the specimen is processed is set in this way, the operator operates the stage controller 68 to shift the Y2-motion stage 53 in such a way that this stage 53 is placed on the optic axis I of the ion beam generator 63 while the positional relation between the ion beam-blocking wire 61 and the specimen is maintained. Then, the operator operates the ion beam controller 69 to tilt the ion beam generator 63 several degrees, as shown in FIG. 20(A). He then operates the ion beam controller 69 to cause the ion beam generator 63 to emit the ion beam for a given time, thus etching the specimen S, as shown in FIG. 20(B) As shown, a non-etched portion St has side surfaces $Sf_1$ and $Sf_2$. The side surface $Sf_1$ is substantially parallel to a side surface $S_{s1}$ of the specimen S but the side surface $S_{f2}$ is not parallel to the side surface $S_{s1}$. The mechanism by which the specimen is etched in this way is next described by referring to FIG. 21.

Figure 21:
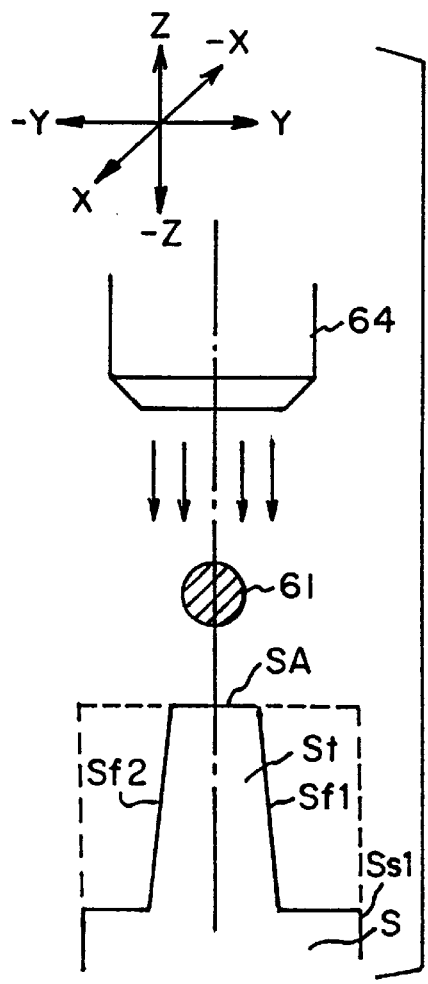

Referring to FIG. 21, it has been experimentally confirmed that if the ion beam is emitted in a direction parallel to the specimen S when the ion beam generator 63 is not tilted, the non-etched portion St of the specimen S assumes a trapezoidal cross section. Accordingly, as shown in FIG. 20(B), if the ion beam is directed at the specimen at an angle determined, taking account of the tilts of the oblique sides of the trapezoid, then the right side surface $Sf_1$ created by the contribution of one side fringe or edge 61c of the wire 61 becomes substantially parallel to the side surface $S_{s1}$ of the specimen S.

Figure 20C:
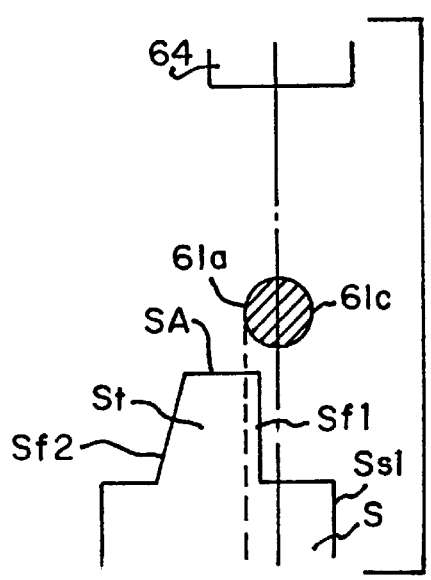

After the first etching of the specimen is completed, the operator operates the stage controller 68 to move the Y2-motion stage 53 in such a way that the wire 61 and the specimen are brought immediately under the TV camera 64. Then, while watching the display device 65, he operates the stage controller 68 to move the Y1-motion/tilt stage 56 in the Y-direction in such a manner that the edge 61a of the wire 61 is brought into a desired position on the non-etched portion St, as shown in FIG. 20(C) Thus, a portion of interest on the non-etched portion St is hidden by the wire.

Figure 20D:
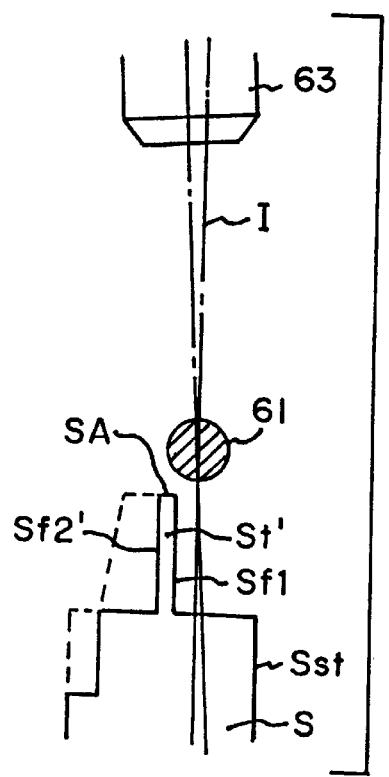

When the setting of the processing position for the specimen is completed in this way, the operator operates the stage controller 68 to move the Y2-motion stage 53 in such a way that the ion beam-blocking wire 61 and the specimen are brought to the optic axis I. Then, he operates the ion beam controller 69 to tilt the ion beam generator 63 several degrees in a direction opposite to the direction used during the first etching step, as shown in FIG. 20(D) After the ion beam generator 63 has tilted, he operates the ion beam controller 69 to cause the ion beam generator 63 to emit the ion beam for a given time. The produced ion beam etches the specimen S, as shown in FIG. 20(D).

During this second etching step, the ion beam generator 63 has tilted in a direction opposite to the direction adopted during the first etching. Therefore, the left side surface $S_{f2}'$ of the non-etched portion St' becomes nearly parallel to the side surface $S_{s1}$ of the specimen S As a result, a quite thin specimen St' having parallel side surfaces can be obtained, the specimen being adapted for electron microscopy.

While the operation of the apparatus shown in FIG. 18 has been described, the X-tilt stage 55 may be rotated instead of tilting the ion beam generator 63. In this case, the specimen is inclined with respect to the ion beam IB, thus producing similar effects. Furthermore, instead of the TV camera 64, a scanning electron microscope may be mounted.

Figure 22:
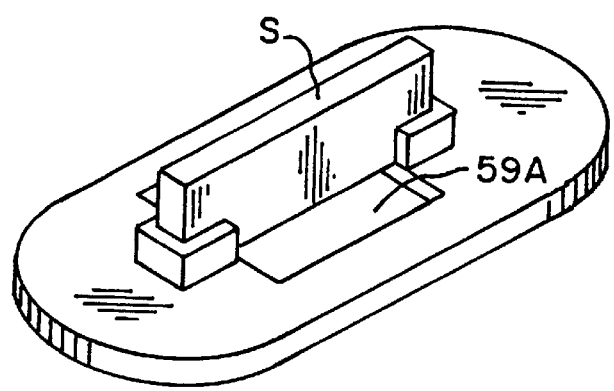
FIG. 22 is a perspective view of a specimen holder shown in FIG. 18.

Referring to FIG. 22, the aforementioned specimen holder 59 may be provided with a hole 59A permitting passage of the ion beam After the ion beam has passed by the specimen S, if the beam is made to pass through the hole 59A, then thermal drift of the specimen due to temperature rise of the specimen holder 59 caused by the ion beam irradiation can be prevented. Hence, a better specimen adapted for electron microscopy can be obtained.

Figure 23A:
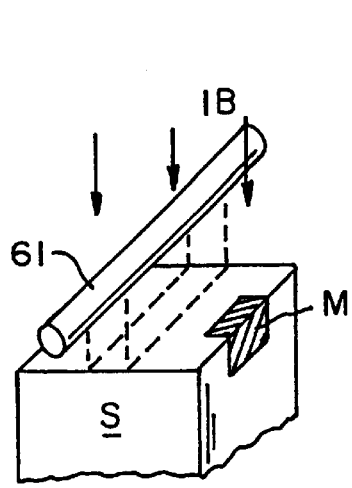
FIGS. 23 and 24 are perspective views of specimens etched by an ion beam.
Figure 23B:
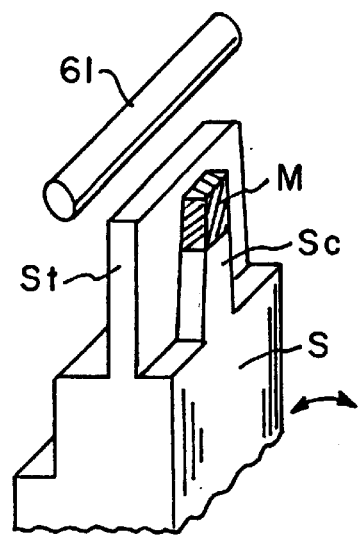
Figure 24:
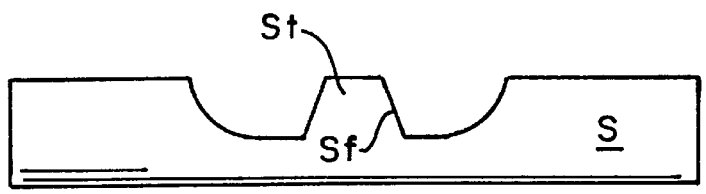

If the specimen S contains a substance M which cannot be easily etched by the ion beam, as shown in FIG. 23(A), a portion hidden by this substance is not etched away but rather left behind. After the etching, the specimen assumes a form as shown in FIG. 23(B). Under this condition, the non-etched portion St cannot be observed by the electron microscope. However, this problem can be solved by performing etching while tilting the specimen forward and backward alternately and repeatedly by means of the Y-tilt stage 54, as indicated by the arrows in FIG. 23(B). In consequence, a non-etched portion Sc hidden by the substance M is etched. As a result, the substance M can be separated from the specimen. The tilt angle of the Y-tilt stage 54 and the tilt rate can be appropriately selected.

Where a relatively large specimen cross section is observed by a scanning electron microscope, a good specimen can be prepared, using the apparatus shown in FIG. 18. In this case, this specimen can be prepared simply by subjecting the specimen to the first etching step. FIG. 24 is a cross-sectional view of a specimen prepared in this way. If such a specimen is set in a scanning electron microscope, an etched surface Sf of the non-etched portion St can be scanned with an electron beam and thus the cross section can be observed.

What is claimed is:

1. A method of preparing a specimen, comprising the steps for:

evacuating the interior of a specimen-processing chamber;

placing a specimen in said specimen-processing chamber at a location where an etching beam impinges on said specimen;

preparing a beam-blocking member having a first linear edge and a second linear edge which is substantially parallel to said first linear edge;

placing said beam-blocking member close to a surface of said specimen to be processed such that said beam-blocking member blocks a part of the beam impinging on said specimen;

performing a first etching step by directing the beam at the specimen via said beam-blocking member to cause said first edge to create an irradiated region and a nonirradiated region on the specimen;

producing a relative movement between said specimen and said beam-blocking member in such a way that said second edge is brought onto said nonirradiated region; and then performing a second etching step by directing said beam at the specimen via said specimen-blocking member to create a protruded region that is put between a first boundary line and a second boundary line on the specimen, said first boundary line being created by a contribution of said first edge, said second boundary line being created by a contribution of said second edge.

2. The method of claim 1, wherein the processed surface of said specimen has a larger dimension and a smaller dimension, and wherein said beam impinging on said specimen has a diameter large enough to simultaneously etch a region of a width exceeding half of said smaller dimension of said processed surface.

3. The method of claim 1 or 2, wherein said first and second etching steps are carried out while reciprocating said first and second edges relative to the beam-blocking member in their longitudinal direction.

4. The method of claim 3, wherein said step of producing a relative movement between said specimen and said beam-blocking member between said first and second etching steps consists of rotating said specimen and said beam-blocking member relative to each other in such a way that said wire intersects said nonirradiated region created by said first etching step.

5. The method of claim 1 or 2, wherein said irradiated portion of said beam-blocking member is made of an amorphous metal.

6. The method of claim 1 or 2, wherein said beam-blocking member is spaced from said specimen by a distance of less than 10 micrometers.

7. The method of claim 1 or 2, wherein said beam-blocking member is made of one wire.

8. The method of claim 7, wherein said wire has a circular cross section.

9. The method of claim 8, wherein the cross section of said wire has a diameter of 10 micrometers to hundreds of micrometers.

10. The method of claim 7, wherein said wire has a rectangular cross section.

11. The method of claim 7, wherein said wire is moved in its longitudinal direction.

12. The method of claim 1 or 2, wherein said beam-blocking member has a rectangular hole.

13. A specimen preparation apparatus comprising:
a specimen-processing chamber whose interior is evacuated by an evacuating machine;
a specimen stage which is placed inside said specimen-processing chamber and on which a specimen is placed;
a beam generator for producing an etching beam to a surface of said specimen to be processed;
a beam-blocking member comprising a wire having a first linear edge and a second linear edge that is substantially parallel to said first edge, said beam-blocking member being placed close to said processed surface of said specimen so as to block a part of the beam directed at said specimen creating an irradiated and a nonirradiated region and such that said first edge defines the boundary between the blocked and unblocked beam; and
a first moving mechanism for producing a relative movement between said specimen and said beam-blocking member such that a previously nonirradiated region is irradiated and such that said second edge defines the boundary between the blocked and unblocked beam.

14. The specimen preparation apparatus of claim 13, further comprising an observation means permitting one to observe the position of said specimen relative to said beam-blocking member from the same side as said beam generator.

15. The specimen preparation apparatus of claim 14, further comprising a second moving mechanism for moving together said specimen stage, said beam-blocking member, and said first moving mechanism from the position hit by said beam into a position where an observation is made with said observation means.

16. The specimen preparation apparatus of claim 14, further comprising an image pickup means for observing the space between said beam-blocking member and said specimen from a direction perpendicular to the direction in which the beam is directed.

17. A specimen preparation apparatus for an electron microscope, comprising:
a specimen-processing chamber whose interior is evacuated by a pumping machine and which is surrounded by a wall member;
a specimen stage holding a specimen thereon, said specimen stage being placed inside said specimen-processing chamber such that a surface of said specimen to be processed is located at a specimen preparation position;
a beam generator capable of directing an etching beam at said processed surface of said specimen, said processed surface of said specimen having a larger dimension and a smaller dimension, said beam having a dimension large enough to simultaneously etch a region of a width exceeding half of said smaller dimension of said processed surface;
a beam-blocking member comprising a wire placed close to said processed surface of said specimen so as to cross said beam impinging on said processed surface of said specimen, said beam-blocking member blocking a part of said beam to thereby form a nonirridated region and at least one irradiated region in said processed surface of said specimen; and
a means for moving said specimen stage and said beam-blocking member relative to each other to translate or rotate a boundary line between said nonirradiated region and said irradiated region in said processed surface within a place perpendicular to said beam such that a previously nonirradiated region is irradiated.

18. A method of preparing a specimen for use in an electron microscope, said method comprising the steps of:
evacuating the interior of a specimen-processing chamber;
placing a specimen in said specimen-processing chamber at a specimen preparation position in such a way that a surface of said specimen to be processed is held normal to an incident etching beam;
preparing a beam-blocking member for blocking a part of said beam to create one nonirradiated region in said processed surface of said specimen;
placing said beam-blocking member close to said processed surface of said specimen so as to cross the beam impinging on said processed surface;
performing a first etching step by directing the beam at the specimen via said beam-blocking member to etch said processed surface;
producing a relative movement between said specimen and said beam-blocking member within a plane perpendicular to said beam to block the beam from hitting an elongated portion of said nonirradiated region which was not irradiated with the beam during said first etching step; and
directing the beam at said processed surface of said specimen to etch said processed surface excluding said elongated portion.

* * * * *